United States Patent [19]

Nielsen et al.

[11] Patent Number: 5,731,280
[45] Date of Patent: Mar. 24, 1998

[54] RECOMBINANT LIPASE AND ALPHA-AMYLASE VARIANTS

[75] Inventors: Egon Nielsen; Grethe Rasmussen, both of Copenhagen; Torben Halkier, Frederiksberg, all of Denmark

[73] Assignee: Novo Nordisk A/S, Bagsvaerd, Denmark

[21] Appl. No.: 448,540

[22] PCT Filed: Dec. 22, 1993

[86] PCT No.: PCT/DK93/00441

§ 371 Date: Jun. 15, 1995

§ 102(e) Date: Jun. 15, 1995

[87] PCT Pub. No.: WO94/14951

PCT Pub. Date: Jul. 7, 1994

[30] Foreign Application Priority Data

Dec. 23, 1993 [DK] Denmark ................... 1542/92

[51] Int. Cl.$^6$ ................... C11D 3/386; C12N 9/32
[52] U.S. Cl. ................... 510/392; 510/530; 435/198; 435/200; 435/201; 435/202; 435/203; 435/204
[58] Field of Search ................... 252/174.52, 95; 435/198, 200, 201, 202, 203, 204; 510/392, 530

[56] References Cited

U.S. PATENT DOCUMENTS

| | | | |
|---|---|---|---|
| 4,810,414 | 3/1989 | Huge-Jensen | 252/174.12 |
| 5,030,240 | 7/1991 | Wiersema et al. | 8/111 |
| 5,108,457 | 4/1992 | Poulose et al. | 8/111 |

FOREIGN PATENT DOCUMENTS

| | | |
|---|---|---|
| 0 179 486 | 10/1985 | European Pat. Off. |
| 0305216 | 3/1989 | European Pat. Off. |
| 0 407 225 | 7/1990 | European Pat. Off. |
| 8909813 | 10/1989 | WIPO |
| WO 91/00353 | 6/1990 | WIPO |
| 9105839 | 2/1991 | WIPO |
| WO 92/18683 | 4/1992 | WIPO |
| WO 92/18687 | 4/1992 | WIPO |
| 9211348 | 7/1992 | WIPO |
| WO 93/11254 | 11/1992 | WIPO |

*Primary Examiner*—Paul Lieberman
*Assistant Examiner*—Kery A. Fries
*Attorney, Agent, or Firm*—Steve T. Zelson, Esq.; Cheryl H. Agris, Esq.

[57] ABSTRACT

The present invention relates to lipase and α-amylase variants, stabilized towards the inactiviation caused by peroxidase systems, in which variants a naturally occurring tryosine residue has been deleted, substituted with a different amino acid residue at one or more positions. The invention also relates to a method of stabilizing a lipase or an α-amylase towards the inactivation caused by the preoxidase systems, and detergent compositions comprising a lipase and/or α-amylase variant of the invention.

13 Claims, No Drawings

RECOMBINANT LIPASE AND ALPHA-AMYLASE VARIANTS

CROSS REFERENCE TO RELATED APPLICATIONS

This application is a continuation of PCT/DK93/00441 filed Dec. 22, 1993, which is incorporated herein by reference.

TECHNICAL FIELD

The present invention relates to lipase and α-amylase variants, stabilized towards the inactivation caused by peroxidase systems, in which lipase and α-amylase variants a naturally occurring tyrosine residue has been deleted or substituted with a different amino acid residue at one or more positions.

The invention also relates to a method of stabilizing a lipase or an α-amylase towards the inactivation caused by peroxidase systems, and detergent compositions comprising a lipase and/or an α-amylase variant of the invention.

BACKGROUND ART

Peroxidases (E.C. 1.11.1.7) are enzymes that catalyse the oxidation of a substrate (an electron or hydrogen donor) with hydrogen peroxide. Such enzymes are known from microbial, plant and animal origins, e.g. peroxidase from *Coprinus cinereus* (cf. e.g. EP Patent Application 179,486). They are typically hemoproteins, i.e. they contain a heme as a prosthetic group.

Use of peroxidase together with hydrogen peroxide or a hydrogen peroxide precursor has been suggested e.g. in bleaching of pulp for paper production, in treatment of waste water from pulp production, for improved bleaching in laundry detergents, for dye transfer inhibition during laundering, and for lignin modification, e.g. in particle board production.

Peroxidase systems (also designated POD systems) comprising a peroxidase or a compound exhibiting peroxidase activity, a source of hydrogen peroxide, and a peroxidase enhancing agent, are used for preventing coloured substances, which leach from dyed fabrics, to deposit on other fabrics present in the same wash (this phenomenon is commonly known as dye transfer). Detergent compositions or wash liquors comprising such peroxidase systems have been described in e.g. International Patent Applications WO 92/18687 and WO 92/18683.

A major drawback in applying such peroxidase systems to detergent compositions is that the enzymes present in such compositions may be strongly affected by the peroxidase system, thereby hampering the washing performance of the detergent composition.

SUMMARY OF THE INVENTION

It has now surprisingly been found that lipases and α-amylases may be stabilized towards inactivation caused by peroxidase systems, by deletion or substitution of one or more naturally occurring tyrosine residues with a different amino acid residue.

Accordingly, the invention provides a lipase and/or an α-amylase variant, in which one or more naturally occurring tyrosine residues have been deleted or substituted with a different amino acid residue.

In another aspect, the invention provides a method of stabilization of a lipase and/or an α-amylase variant towards inactivation caused by a peroxidase system, in which method one or more naturally occurring tyrosine residues are deleted or substituted with a different amino acid residue.

In a further aspect, the invention provides detergent compositions comprising a lipase and/or an α-amylase variant of the invention.

In a yet further aspect, the invention provides detergent additives comprising a lipase and/or an α-amylase variant of the invention.

DETAILED DISCLOSURE OF THE INVENTION

The present invention provides novel lipase and α-amylase variants, stabilized towards inactivation caused by peroxidase systems.

In the context of this invention, a stabilized lipase or α-amylase variant is a lipase or an α-amylase having improved stability towards inactivation caused by peroxidase systems, when compared to the parent lipase or α-amylase.

Amino Acids

As abbreviations for amino acids the following symbols are used:

| | | |
|---|---|---|
| A = | Ala = | Alanine |
| C = | Cys = | Cysteine |
| D = | Asp = | Aspartic acid |
| E = | Glu = | Glutamic acid |
| F = | Phe = | Phenylalanine |
| G = | Gly = | Glycine |
| H = | His = | Histidine |
| I = | Ile = | Isoleucine |
| K = | Lys = | Lysine |
| L = | Leu = | Leucine |
| M = | Met = | Methionine |
| N = | Asn = | Asparagine |
| P = | Pro = | Proline |
| Q = | Gln = | Glutamine |
| R = | Arg = | Arginine |
| S = | Ser = | Serine |
| T = | Thr = | Threonine |
| V = | Val = | Valine |
| W = | Trp = | Tryptophan |
| Y = | Tyr = | Tyrosine |
| B = | Asx = | Asp (D) or Asn (N) |
| Z = | Glx = | Glu (E) or Gln (Q) |
| X = | | an arbitrary amino acid |
| * = | | deletion or absent amino acid |

Peroxidase Activity

In the context of this invention, the enzymatic activity of peroxidases is expressed in "Peroxidase Units" (PODU). In the presence of hydrogen peroxide peroxidases (E.C. 1.11.1.7) catalyse the dehydrogenation of 2,2'-azino-bis (3-ethylbenzothiazoline-6-sulfonate) (ABTS). The greenish-blue colour produced is monitored photometrically at 418 nm. One PODU is the amount of enzyme which, under standard conditions (i.e. pH 7.0; hydrogen peroxide as substrate; 0.1 M phosphate buffer; an incubation temp. of 30° C.; an incubation time of 3 min. measured kinetically) catalyses the conversion of 1 μmol of hydrogen peroxide per minute.

Lipase Activity

In the context of this invention, the enzymatic activity of lipases is expressed in Lipase Units. A Lipase Unit (LU) is the amount of enzyme which under standard conditions, i.e. 30.0° C.; pH 7.0; tributyrine substrate, liberates 1 μmol titratable butyric acid per minute.

α-amylase Activity

The α-amylase activity is measured as absorption/ml at 620 nm using Phadebas tablets (Phadebasv® Amylase Test; Pharmacia Diagnostics, SW). The assay is carried out at 60° C.

Peroxidase Systems

In the context of this invention, a peroxidase system is a system comprising a peroxidase or a compound exhibiting peroxidase activity, a source of hydrogen peroxide, and a peroxidase enhancing agent. Such peroxidase systems have been used for obtaining a dye transfer inhibition and have been described in e.g. International Patent Applications WO 92/18687 and WO 92/18683.

In such a peroxidase system, the peroxidase or the compound exhibiting peroxidase activity may be any peroxidase comprised by the enzyme classification EC 1.11.1.7, or any fragment derived therefrom, exhibiting peroxidase activity, or synthetic or semisynthetic derivatives thereof (e.g. porphyrin ring systems or microperoxidases, cf. e.g. U.S. Pat. No. 4,077,768, EP Patent Application 537,381, International Patent Applications WO 91/05858 and WO 92/16634). Such peroxidases are known from microbial, plant and animal origins.

The peroxidase may be producible by plants (e.g. horseradish or soy bean peroxidase) or microorganisms such as fungi or bacteria. Some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens*, *Trichoderma resii*, *Myrothecium verrucana* (IFO 6113), *Verticillum alboatrum*, *Verticillum dahlie*, *Arthromyces ramosus* (FERM P-7754), *Caldariomyces fumago*, *Ulocladium chartarum*, *Embellisia alli* or *Dreschlera halodes*.

Other preferred fungi include strains belonging to the subdivision Basidiomycotina, class Basidiomycetes, e.g. Coprinus, Phanerochaete, Coriolus or Trametes, in particular *Coprinus cinereus* f. microsporus (IFO 8371), *Coprinus macrorhizus*, *Phanerochaete chrysosporium* (e.g. NA-12) or Trametes (previously called Polyporus), e.g.*T. versicolor* (e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium*

Other preferred bacteria include *Bacillus pumilus* (ATCC 12905), *Bacillus stearothermophilus*, *Rhodobacter sphaeroides*, *Rhodomonas palustri*, *Streptococcus lactis*, *Pseudomonas purrocinia* (ATCC 15958) or *Pseudomonas fluorescens* (NRRL B-11).

Further preferred bacteria include strains belonging to Myxococcus, e.g. *M. virescens*.

Other potential sources of useful particular peroxidases are listed in Saunders B C, op. cit., pp. 41–43.

The peroxidase may furthermore be one which is producible by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase and recovering the peroxidase from the culture.

Particularly, a recombinantly produced peroxidase is a peroxidase derived from a Coprinus sp., in particular *C. macrorhizus* or *C. cinereus* according to WO 92/16634.

In the context of this invention, compounds exhibiting peroxidase activity comprise peroxidase active fragments derived from cytochromes, hemoglobin or peroxidase enzymes, and synthetic or semisynthetic derivatives thereof, e.g. iron porphins, iron porphyrins, and iron phthalocyanine and derivatives thereof.

In a peroxidase system, the enhancer may be an oxidizable substrate e.g. metal ions or phenolic compounds such as 7-hydroxycoumarin (7HCm), vanillin (VAN), and p-hydroxybenzenesulfonate (pHBS), described in e.g. International Patent Applications WO 92/18683 and WO 92/18687, and Kato M and Shimizu S, Plant Cell Physiol. 1985 26 (7), pp. 1291–1301 (cf. Table 1 in particular), and Saunders B C, et al., Peroxidase, London, 1964, p. 141 ff. or 2,2'-azino-bis (3-ethylbenzothiazoline-6-sulfonate) (ABTS), described in applicant's copending DK Patent Application No. 9201441.

Lipases

In a preferred embodiment, the lipase of the invention is obtainable from a strain of Humicola, e.g. *H. lanuginosa, H. brevispora, H. brevis* var. *thermoidea*, or *H. insolens*. Lipases obtainable from Humicola are described in e.g. U.S. Pat. No. 4,810,414, EP Application 305,216 and International Patent Application WO 89/01969, which publications are hereby included by reference.

In another specific embodiment, the lipase is obtainable from a strain of Pseudomonas, e.g. *Ps. cepacia, Ps. fragi, Ps. stutzeri*, or *Ps. fluorescens*.Lipases obtainable from Pseudomonas are described in e.g. International Patent Publication 89/04361, which publication is hereby included by reference.

In a third specific embodiment, the lipase is obtainable from a strain of Fusarium, e.g. *F. oxysporum*. Lipases obtainable from Fusarium are described in e.g. EP Publication 130,064 and EP Publication 395,678, which publications are hereby included by reference.

In further specific embodiments, the lipase is obtainable from a strain of Rhizomucor, e.g. *Rhizomucor miehei*,or a strain of Candida, e.g. *C. antarctica*, or *C. cylindracea* (also called *C. rugosa*), or a strain of Chromobacterium, e.g. *C. viscosum*.

In a more preferred embodiment, a lipase variant of the invention is a *Humicola lanuginosa* lipase having an amino acid sequence as described in EP Publication 305,216 (in which publication the amino acid sequence is presented in FIG. 5), which sequence has been changed in one or more of the following positions: 16, 21, 53, 138, 164, 171, 194, 213, 220, 261.

Amylases

In a preferred embodiment, the α-amylase variant of the invention is obtainable from a strain of Bacillus or a strain of Aspergillus.

In a more specific embodiment, the α-amylase variant is obtainable from a strain of *B. licheniformis*. The amino acid sequence for the *B. licheniformis* 584 α-amylase (Stephens et al.) appears from *J. Bacteriol.* 1984 158 369–372, and *J. Bacteriol.* 166, 635–643, 1986, FR 2665178 or EP 410498. Thus, the tyrosine positions are: 10, 14, 31, 46, 56, 59, 62, 77, 98, 150, 158, 175, 193, 195, 198, 203, 219, 262, 273, 290, 302, 348, 358, 363, 367, 394, 396, 402, 439, 480.

In another specific embodiment, the α-amylase variant is obtainable from a strain of *B. amyloliquefaciens*. The amino acid sequence for the *B. amyloliquefaciens* α-amylase (Takkinen et al.) appears from *J. Biol Chem.* 1983 258 1007–1013.

In a third specific embodiment, the α-amylase variant is obtainable from a strain of *B. stearothermophilus*. The amino acid sequence for the *B. stearotherophilus* α-amylase appears from *J. Bacteriol.* 166, 635–643, 1986.

In a fourth specific embodiment, the α-amylase variant is obtainable from a strain of *A. niger*. The amino acid sequence for the *A. niger* α-amylase appears from DK Patent Application 5126/87.

In further specific embodiments, α-amylase variants of the invention are chimeric α-amylases. Chimeric α-amylases are disclosed in e.g. EP Patent Publication 252,666.

Methods of Stabilizing Lipases and α-amylases

The present invention provides a method of stabilizing lipases and α-amylases towards inactivation caused by peroxidase systems, by which method one or more naturally occurring tyrosine residues are deleted or substituted with a different amino acid residue.

Recombinantly Produced Lipases and α-amylases

In the past, numerous processes have been developed for the production of polypeptides or proteins by means of the recombinant DNA technology. Mostly used for this purpose are *E. coli, Bacillus subtilis, Saccharomyces cerevisiae* and different Aspergillus strains, e.g. *A. oryzae* and *A. niger.* Especially the Aspergillii are attractive candidates as host microorganisms for recombinant DNA vectors being well-characterized and widely used microorganisms for the commercial production of enzymes. In *Aspergillus oryzae*, methods have been developed for transformation of the organism, and production of several enzymes, among these the *Humicola lanuginosa* and *Rhizomucor miehei* lipases (vide e.g. European Patent Applications 238,023 and 305,216, and International Patent Application WO 89/01969), which publications are hereby included by reference.

Expression of Polypeptides Biosynthetically

Upon transformation of an organism where the intention is production of a polypeptide or a protein, a DNA sequence is introduced into the organism. The sequence contains the coding region of the gene of interest flanked by transcription/translation start signals and transcription/translation termination signals. The coding region contains units of three base pairs, called codons, which upon translation of the transcribed gene are translated into amino acids, which again are assembled to give the polypeptide of interest.

Introducing Mutations in Polypeptides

By changing one or more specific codons in the coding region and transforming the host microorganism with these new coding regions, new polypeptides can be produced which differ from the original polypeptide by one or more amino acids. Such alterations can be introduced by means of a technique generally known as "site-directed in vitro mutagenesis". A number of methods have been published. An early method is described by Zoller & Smith, DNA 1984 3 (6) 479–488, and involves use of the single-stranded M13 bacteriophage. A preferred method using PCR (polymerase chain reaction) is described by Nelson & Long, Analytical Biochemistry, 1989 180 147–151. It involves a 3-step generation of a PCR fragment containing the desired mutation by using a chemically synthesized DNA oligonucleotide as one of the primers in the PCR reactions. From the PCR-generated fragment, a DNA fragment carrying the mutation can be isolated by cleavage with restriction enzymes and re-inserted into the expression plasmid. A third mutagenesis method takes advantage of restriction sites in the DNA coding region. By digesting the DNA with restriction enzymes at sites flanking the mutagenesis target, synthesizing a new fragment synthetically containing the desired mutation and cloning this new fragment between the restriction sites, a mutant coding region can be constructed.

All methods are generally applicable to investigations in the field called protein engineering which deals with the development of polypeptides with new or altered characteristics.

Transformation and expression may be accomplished by methods known in the art, e.g. as described in European Patent Application 305,216, which specification is hereby included by reference.

The microorganisms able to produce a stabilized lipase or α-amylase of this invention can be cultivated by conventional fermentation methods in a nutrient medium containing assimilable carbon and nitrogen together with other essential nutrients, the medium being composed in accordance with the principles of the known art. Purification and recovery of the stabilized lipase or α-amylase may also be conducted in accordance with methods known per se.

Nucleotide Sequences, Expression Vectors And Microorganisms

This invention also relates to DNA nucleotide sequences encoding a stabilized lipase or α-amylase of the invention. The stabilized lipase or α-amylase may be expressed and produced when DNA nucleotide sequence encoding the lipase or α-amylase is inserted into a suitable vector in a suitable host organism. The host organism is not necessarily identical to the organism from which the parent gene originated. The construction of the mutated genes, vectors and mutant and transformed microorganisms may be carried out by any appropriate recombinant DNA technique, known in the art.

The invention also relates to expression vectors and host organisms containing a DNA nucleotide encoding a stabilized lipase or α-amylase of this invention.

Detergent Compositions

According to the invention, the lipase and the α-amylase variant may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40 % of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, alkyl-(N-methyl)-glucoseamide or polyhydroxy alkyl fatty acid amide (e.g. as described in WO 92/06154).

The detergent composition may additionally comprise one or more other enzymes, such as cutinase, protease, cellulase, peroxidase, or oxidase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g $C_{12-18}$ alcohol, 1–2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O, 2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds supressors, perfume, optical brightener, photobleach) | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1–2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O, 2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds supressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O, 2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 1–3% |
| enzymes | 0–5% |
| minor ingredients (e.g. suds supressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O, 2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds supressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds supressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g PEG, PVP) | 0–3% |
| anchoring polymers as e.g. lauryl metharylate/acrylic acid copolymer; molar ratio 25:1; MW 3800 | 0–3% |
| glycerol | 0–5% |
| enzymes | 0–5% |
| minor ingredients (e.g. dispersants, suds supressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as $Na_2CO_3$) | 5–10% |
| soluble silicate (as $Na_2O, 2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds supressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as $Na_2CO_3$) | 4–10% |
| soluble silicate (as $Na_2O, 2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g. PVP, maleic/acrylic acid copolymer, PEG) | 1–5% |
| enzymes | 0–5% |
| minor ingredients (e.g. suds supressors, perfume) | 0–5% |

9) A detergent composition formulated as a granulate comprising

| | |
|---|---|
| linear alkylbenzenesulfonate (calculated as acid) | 6–12% |
| nonionic surfactant | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. $C_{12-15}$ alcohol, 2–3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O$, $2SiO_2$) | 5–15% |
| sodium sulfate (as $Na_2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) where the content of linear alkylbenzenesulfonate—or a part of it—is substituted by alkyl sulfate ($C_{12}$–$C_{18}$).

14) Detergent formulations as described in 1)–13) which contain a stabilized or encapsulated peracid either as an additional component or as a substitute for already specified bleach systems.

15) Detergent compositions as described in 3), 7), 9) and 12) where the content of perborate is substituted by percarbonate.

16) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

The lipase and α-amylase variants of the invention may be incorporated in concentrations conventionally employed in detergents. It is at present contemplated that, in the detergent composition of the invention, the lipase and α-amylase variants may be added in an amount corresponding to 0.001–100 mg of lipase or α-amylase variant per liter of wash liquor.

We claim:

1. A Humicola, Pseudomonna, Fusarium, Rhizomucor, or Candida lipase or a Bacillus or Aspergillus alpha-amylase variant having an improved stability towards inactivation caused by a peroxidase system, said peroxidase system comprising a peroxidase or a compound exhibiting peroxidase activity, a source of hydrogen peroxide and a peroxidase enhancing agent, as compared to a parent lipase or alpha-amylase, in which one or more naturally occurring tyrosine residues in said lipase or alpha-amylase variant has been substituted with an amino acid residue selected from the consisting of phenylalanine, leucine, isoleucine, valine, glutamine, asparagine, serine, threonine, glutamic acid, and histidine.

2. The lipase variant according to claim 1 in which said lipase variant is a H. lanuginosa, H. brevispora, H. brevis var. thermoidea, H. insolens, Ps. cepacia, Ps. fragi, Ps. stutzeri, Ps. fluorescens, F. oxysporum, Rhizomucor miehei, C. antarctica, or C. cylindracea variant.

3. The lipase variant of claim 1 in which said lipase variant is a H. lanuginosa lipase variant and in which a naturally occurring tyrosine residue in said lipase variant is at one or more of the positions selected from the group consisting of 16, 21, 53, 138, 164, 171, 194, 213, 220, and 261.

4. The alpha-amylase variant of claim 1 in which said alpha-amylase variant is a B. licheniformis alpha-amylase variant and in which a naturally occurring tyrosine residue in said alpha-amylase variant has been substituted at one or more of the positions selected from the group consisting of 10, 14, 31, 46, 59, 62, 77, 98, 150, 158, 175, 193, 195, 198, 203, 219, 262, 273, 290, 302, 348, 358, 363, 367, 394, 396, 402, 439, and 480.

5. A method of stabilizing a Humicola, Pseudomenus, Fusarium, Rhizomucor, or Candida lipase variant or Bacillus or Aspergillus alpha-amylase variant toward peroxidase inactivation as compared to a parental lipase or alpha-amylase comprising substituting one or more naturally occurring tyrosine residues in said lipase or alpha-amylase variant with an amino acid residue selected from the group consisting of phenylalanine, leucine, isoleucine, valine, glutamine, asparagine, serine, threonine, glutamic acid, and histidine.

6. The method according to claim 5 in which the inactivation occurs in a peroxidase a system comprising a peroxidase or a compound exhibiting peroxidase activity, a source of hydrogen peroxide, and a peroxidase enhancing agent.

7. The method according to claim 5 in which said lipase variant is H. lanuginosa, H. brevispora, H. brevis var. thermoidea, H. insolens, Ps. cepacia, Ps. fragi, Ps. stutzeri, Ps. fluorescens, F. oxysporum, Rhizomucor miehei, C. antarctica, or C. cylindracea lipase variant.

8. The method according to claim 5 in which said lipase variant is a H. Lanuginosa lipase variant and in which one or more naturally occurring tyrosine residues in said lipase variant is substituted at one or more of the positions selected from the group consisting of 16, 21, 53, 138, 164, 171, 194, 213, 220, and 261.

9. The method according to claim 5 in which said B. licheniformis alpha-amylase variant and in which one or more naturally occurring tyrosine residues in said alpha-amylase variant is substituted at one or more of the positions selected from the group consisting of 10, 14, 31, 46, 56, 59, 62, 77, 98, 150, 158, 175, 193, 195, 198, 203, 219, 262, 273, 290, 302, 348, 358, 363, 367, 394, 396, 402, 439, and 480.

10. A detergent composition comprising the lipase or alpha-amylase variant of claim 1.

11. The detergent composition of claim 10 in which said composition comprises another enzyme.

12. The detergent composition of claim 10 in which said composition comprises another enzyme selected from the group consisting of a protease, cellulase, oxidase and peroxidase.

13. The detergent composition of claim 10 formulated in a form selected from the group consisting of a non-dusting granulate, a stabilized liquid, a slurry, and a protected enzyme.

* * * * *